United States Patent [19]

Gerwick, III

[11] Patent Number: 4,586,949
[45] Date of Patent: May 6, 1986

[54] SELECTIVE, BROADSPECTRUM WEED CONTROL IN SOYBEANS

[75] Inventor: B. Clifford Gerwick, III, Concord, Calif.

[73] Assignee: The Dow Chemical Company, Midland, Mich.

[21] Appl. No.: 595,786

[22] Filed: Apr. 2, 1984

Related U.S. Application Data

[63] Continuation of Ser. No. 435,194, Oct. 19, 1982, abandoned.

[51] Int. Cl.4 ............................................. A01N 43/88
[52] U.S. Cl. ............................................ 71/91; 71/94
[58] Field of Search ..................................... 71/91, 94

[56] References Cited

U.S. PATENT DOCUMENTS

| | | | |
|---|---|---|---|
| 3,826,642 | 7/1974 | Fischer | 71/92 |
| 3,935,000 | 1/1976 | Fischer | 71/92 |
| 3,940,389 | 2/1976 | McKendry et al. | 71/91 |
| 4,030,909 | 6/1977 | Fischer | 71/92 |
| 4,311,513 | 1/1982 | Bohner et al. | 71/92 |
| 4,322,241 | 3/1982 | Pissiotas et al. | 71/94 |

FOREIGN PATENT DOCUMENTS

| | | | |
|---|---|---|---|
| 118402 | 9/1980 | Japan | 71/92 |
| 189795 | 11/1981 | New Zealand | 71/94 |

OTHER PUBLICATIONS

ICI PP009 Product Bulletin (1980).
Cartwright, "Herbicidal 2-(4-Alkoxy-) etc.;" (1979) CA 92, No. 58618y (1980).
Dow, "(Trifluoromethyl) Pyridyl etc.;" (1979) CA 93, No. 168132p (1980).
Anon, "Inhibiting the Antagonism etc.;" (1982) CA 97, No. 140150b (1982).
Anon. Chem. Abst., vol. 97 (1982) 140150b.

Primary Examiner—Catherine L. Mills
Attorney, Agent, or Firm—Edward E. Schilling; Ronald G. Brookens

[57] ABSTRACT

Less damage to soybeans occur when the combination of bentazon and a 3-substituted-pyridyloxy(or thio)phenoxy alkanoate herbicide is applied thereto, in comparison to the combination of bentazon and a 3-unsubstituted pyridyloxy(or thio)phenoxy alkanoate herbicide.

14 Claims, No Drawings

SELECTIVE, BROADSPECTRUM WEED CONTROL IN SOYBEANS

This is a continuation of application Ser. No. 435,194, filed Oct. 19, 1982, now abandoned.

BACKGROUND OF THE INVENTION

The present invention relates to an improved method of selectively controlling grassy weeds and broadleaf weeds in soybean crops.

2-Pyridyloxy(or thio)phenoxy alkanoate grass herbicides are well known herbicides and are described, for example, in Belgium Patent 868,875; PCT Application WP 7900094; EPO Application 483; U.S. Pat. No. 4,213,774; and French Pat. No. 7522436. These grass herbicides are useful for selectively controlling annual and perennial grassy weeds in the presence of desirable broadleaf crops.

Benzothiadiazinone derivatives, described in U.S. Pat. Nos. 4,015,130; 4,116,672; 4,155,746; 3,940,389; 3,708,277 and 3,621,017 are useful as herbicides and especially as broadleaf active herbicides.

Pyridyloxy(or thio)phenoxy alkanoate herbicides are typically applied post-emergently in the presence of nonionic surfactants. To extend the weed control spectrum in a given application, it has been taught that pyridyloxy(or thio)phenoxy alkanoate herbicides be mixed with benzothiadiazinone broadleaf active herbicides and thereafter applied to unwanted vegetation to provide a broad spectrum herbicidal composition effective against grasses and broadleaf weeds. See, for example, New Zealand Patent Specification 189,795 (published Nov. 19, 1981) which teaches combinations of pyridyloxyphenoxy derivatives and other herbicides.

In particular, New Zealand Patent Specification 189,795, teaches combining 2-(4-(2-pyridinyl)oxy)-phenoxy propionate, n-butyl ester, i.e., commonly known as fluazifop-butyl and commercially available as FUSILADE ® herbicide, with bentazon and applying the combination to soybeans for selective broad spectrum weed control. A serious problem associated with the combination of fluazifop-butyl and bentazon when applied to soybean crops is an increase in phytotoxicity to the soybean plants. This is an especially annoying problem in view of the fact that the herbicidal activity to grasses of pyridyloxyphenoxy alkanoate herbicides is decreased when combined with benzothiadiazinone derivatives. In fact, technical literature distributed by the manufacturer of FUSILADE ® herbicide acknowledges the phytotoxicity of the combination of fluazifop-butyl and bentazon towards soybeans and specifically recommends avoidance of the combination being applied to soybean crops.

It has been found unexpectedly that pyridyloxy(or thio)phenoxy alkanoate grass herbicides that have a substituent other than hydrogen in the 3-position of the pyridine ring, when combined with benzothiadiazinone herbicides, exhibit less phytotoxicity or damage to soybean plants when the combination of herbicides is applied thereto, as compared to the combinations wherein the pyridyloxyphenoxy alkanoate herbicide contains hydrogen in the 3-position of the pyridine ring.

SUMMARY OF THE INVENTION

In accordance with the present invention, pyridyloxy(or thio)phenoxy alkanoate herbicides having a substituent in the 3-position of the pyridine ring other than hydrogen, when combined with benzothiadiazinone herbicides, provide an effective broad spectrum herbicidal combination more selective to soybean plants than the above described herbicidal combination wherein the pyridyloxy(or thio)phenoxy alkanoate has hydrogen in the 3-position of the pyridine ring. Suitable substituents that can replace hydrogen in the 3-position of the pyridine ring include Cl, F, Br, I, $CF_3$, $C_1$–$C_4$ alkyl, $C_1$–$C_4$ alkoxy and $NO_2$.

Of particular interest is the combination of bentazon with 2-(4-((3-chloro-5-(trifluoromethyl)-2-pyridyl)oxy)-phenoxy)propionic acid and agriculturally acceptable salts, amides, alcohols, esters including reverse esters and ethers thereof. Also of interest is the combination of bentazon with 2-(4-((3-fluoro-5-(trifluoromethy)-2-pyridyl)oxy)phenoxy)propionic acid and agriculturally acceptable salts, amides, alcohols, esters and ethers thereof. Agriculturally acceptable derivatives of the acids are those salts, amides, alcohols, esters including reverse esters and ethers which possess herbicidal activity while being substantially non-phytotoxic to soybean plants. These herbicidal combinations provide broad spectrum weed control in soybean crops while exhibiting less phytotoxicity toward the soybean plants than the combination of bentazon and fluazifop-butyl, a pyridyloxyphenoxy propanoic acid ester having hydrogen as the substituent in the 3-position of the pyridine ring.

DETAILED DESCRIPTION OF THE INVENTION

The pyridyloxy-phenoxy alkanoate herbicides of the present invention, generally grass active herbicides, are known compounds and include all of the compounds described in Belgium Patent 868,875; PCT Application WP 7900094; EPO Application 483; U.S. Pat. No. 4,213,774 and French Patent 7522436 all of which are incorporated herein by reference. Preferred pyridyloxy-phenoxy alkanoate herbicides include pyridyloxy-phenoxy propionate compounds of the formula

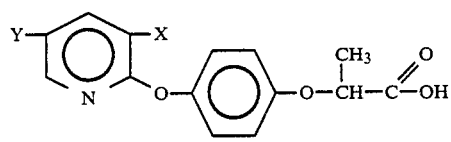

wherein
X represents Cl, F, Br, I, $C_1$–$C_4$ alkyl, $C_1$–$C_4$ alkoxy, $NO_2$ or —$CF_3$;
Y represents Cl, F, Br, I, $C_1$–$C_4$ alkyl, $C_1$–$C_4$ alkoxy, $NO_2$ or —$CF_3$; and agriculturally acceptable salts, esters, alcohols, amides or ethers thereof.

Agriculturally acceptable salts, amides, alcohols, ethers and esters of the above pyridyloxy-phenoxy propionates include compounds of the formula

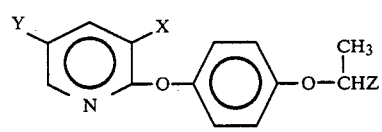

wherein
X and Y are as hereinbefore defined;

Z represents —CO₂H (the acids), —CO₂M, —CO₂R, —COSR, —CONR′₂, —CSNH₂, —CN, —CH₂OR′ or —CH₂O₂CR′;

M represents Na, K, Mg, Ca or N(R″)₄;

R represents $C_1$-$C_8$ alkyl or $C_3$-$C_6$ alkoxyalkyl;

each R′ independently represents H or $C_1$-$C_4$ alkyl; and

R″ independently represents H, $C_1$-$C_4$ alkyl or $C_2$—$C_3$ hydroxyalkyl.

Specific pyridinyloxyphenoxy propionate herbicides within the scope of the present invention include:

2-(4-((3-chloro-5-(trifluoromethyl)pyridyl)-oxy)-phenoxy)propionic acid and agriculturally acceptable salts, alcohols, esters, amides and ethers thereof;

2-(4-((3-fluoro-5-(trifluoromethyl)pyridyl)-oxy)phenoxy)propionic acid and agriculturally acceptable salts, alcohols, esters, amides and ethers thereof;

methyl 2-(4-((3-chloro-5-(trifluoromethyl)-2-pyridinyl)oxy)phenoxy)propionate;

butyl 2-(4-((3-chloro-5-(trifluoromethyl)-2-pyridinyl)oxy)phenoxy)propionate;

ethoxy ethyl 2-(4-((3-chloro-5-(trifluoromethyl)-2-pyridinyloxy)phenoxy)propionate; and 1-methoxy-2-propyl 2-(4-((3-chloro-5-(trifluoromethyl)-2-pyridinyl)oxy)phenoxy propionate;

methyl 2-(4-((3-fluoro-5-(trifluoromethyl)-2-pyridinyl)oxy)phenoxy)propionate;

butyl 2-(4-((3-fluoro-5-(trifluoromethyl)-2-pyridinyl)oxy)phenoxy)propionate;

ethoxy ethyl 2-(4-((3-fluoro-5-(trifluoromethyl)-2-pyridinyl)oxy)phenoxy)propionate; and 1-methoxy-2-propyl 2-(4-((3-fluoro-5-(trifluoromethyl)-2-pyridinyl)oxy)phenoxy)propionate.

The benzothiadiazinone herbicides of the present invention, generally broadleaf active herbicides, are known compounds and include all of the compounds described in U.S. Pat. Nos. 4,051,130; 4,116,672; 4,155,746; 3,940,389; 3,708,277 and 3,621,017, all of which are incorporated herein by reference. Preferred benzothiadiazinone herbicides include those of the formula:

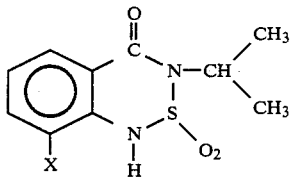

wherein

X represents hydrogen, chloro, bromo, fluoro, $C_1$-$C_8$ alkyl and nitro, and salts thereof.

Specifically preferred benzothiadiazinone herbicides include:

8-chloro-3-(1-methylethyl)-1H-2,1,3-benzothiadiazin-4(3H)-one-2,2-dioxide;

8-nitro-3-(1-methylethyl)-1H-2,1,3-benzothiadiazin-4(3H)-one-2,2-dioxide;

8-fluoro-3-(1-methylethyl)-1H-2,1,3-benzothiadiazin-4(3H)-one-2,2-dioxide;

8-methyl-3-(1-methylethyl)-1H-2,1,3-benzothiadiazin-4(3H)-one-2,2-dioxide; and 3-(1-methylethyl)-1H-2,1,3-benzothiadiazinone-4(3H)-one-2,2-dioxide, commonly known as bentazon.

Bentazon, a broadleaf active herbicide and a preferred compound, is a commercially available product from the BASF Wyandotte Corporation under the trade name BASAGRAN. Bentazon is usually applied to broadleaf weeds at a rate of from about 0.5 to about 1.5 lbs of active ingredient per acre.

In the practice of the present invention the pyridyloxy-phenoxy alkanoate herbicide and the benzothiadiazinone herbicide are formulated into a spray formulation using well known techniques. For example, bentazon, formulated as the water-soluble Na⁺ salt, is mixed in water and thereafter 2-(4-((3-chloro-5-(trifluoromethyl)-2-pyridyl)oxy)phenoxy)propionic acid or an ester thereof, such as the methyl, butyl or ethoxy ethyl ester, is added to the bentazon solution, with agitation, so that a uniform mixture is formed containing both herbicides.

Once prepared the compositions of the present invention are applied to soybean crops employing procedures well known in the art.

In one embodiment of the present invention, the Na⁺ salt of bentazon is combined with an ester or salt of 2-(4-((3-fluoro-5-(trifluoromethyl)-2-pyridyl)-oxy)-phenoxy)propionic acid in an aqueous spray mixture and applied to soybeans for broad spectrum weed control.

In a preferred embodiment of the present invention, the Na⁺ salt of bentazon and an ester of 2-(4-((3-chloro-5-(trifluoromethyl)-2-pyridyl)oxy)phenoxy)propionic acid, formulated as an emulsifiable concentrate, are combined in an aqueous spray mixture in the presence of a surface active agent to facilitate leaf wetting and applied to soybeans for broad spectrum weed control.

The exact amount of herbicide applied in pounds per acre will vary, depending on many factors, such as, for example, the particular herbicides employed, soil conditions, vegetative conditions, climatological conditions to name a few, and is readily determinable by one skilled in the art.

When bentazon, employed as the benzothiadiazinone herbicide, is combined with an ester of 2-(4-((3-chloro-5-(trifluoromethyl)-2-pyridyl)oxy)-phenoxy)propanoic acid, employed as the pyridyloxyphenoxy herbicide, the bentazon is used in amounts to provide from about 0.5 to about 1.5 lbs/acre and the ester of 2-(4-((3-chloro)-5-(trifluoromethyl)-2-pyridyl)oxy)phenoxy)-propanoic acid is present in amounts to provide from about 0.03 to about 0.5 lbs/acre.

The following examples illustrate the practice of the present invention but should not be construed as limiting its scope.

EXAMPLE 1

Various concentrations of fluazifop-butyl (formulated as a 2 lb/gal emulsifiable concentrate) and BASAGRAN ® brand bentazon were combined in an aqueous tank mixture which included ORTHO ® X-77 (0.25% v/v) brand surfactant. The combination was applied in the field to Giant Foxtail (growth stage: 4-6 leaf; 3-5 inches in height) and soybeans (growth stage: 3 trifoliate, 8 inches in height) and evaluated 1 and 2 weeks after treatment for percent control of Giant Foxtail and percent damage to soybeans. Results are listed in Table 1.

TABLE 1

| Run # | Lb Active Ingredient | per acre | % Giant Foxtail Control (Weeks After Treatment) 1 | 2 | % Damage to Soybeans (Weeks After Treatment) 1 | 2 |
|---|---|---|---|---|---|---|
| 1. | fluazifop-butyl | 0.125 lb/A | 68 | 86 | 0 | 0 |
| 2. | fluazifop-butyl bentazon | 0.125 0.75 | 65 | 45 | 30 | 17 |
| 3. | fluazifop-butyl | 0.25 | 73 | 89 | 2 | 5 |
| 4. | fluazifop-butyl bentazon | 0.25 0.75 | 67 | 70 | 30 | 17 |
| 5. | fluazifop-butyl | 0.5 | 75 | 88 | 10 | 6 |
| 6. | fluazifop-butyl bentazon | 0.5 0.75 | 8 | 95 | 40 | 29 |

EXAMPLE 2

Various concentrations of 2-(4-((3-chloro-5-(trifluoromethyl)-2-pyridinyl)oxy)phenoxy)propionate, n-butyl ester (hereinafter "Cpd A") with bentazon were formulated and applied in the field as described in Example 1. The combination was applied in tank mixture to Giant Foxtail (3-6 leaf) and soybeans (1-2 trifoliates) and evaluated 1 and 2 weeks after treatment for percent control of Giant Foxtail and percent damage to soybeans. Results are listed in Table 2.

EXAMPLE 3

Various concentrations of fluazifop-butyl formulated as an emulsifiable concentrate (2 lb/gal) with BASAGRAN® brand bentazon and 2-(4-((3-chloro-5-(trifluoromethyl)-2-pyridinyl)oxy)phenoxy)propionic acid, n-butyl ester (hereinafter "Cpd A") with BASAGRAN® brand bentazon were applied as aqueous mixtures in the presence of ATPLUS® 411F brand crop oil with emulsifiers to greenhouse grown soybeans. The soybeans were in the second (2nd) trifoliate leaf stage at the time of treatment and evaluated for injury 4 days after treatment. Results are listed in Table 3.

TABLE 2

| Run # | Lb active ingredient per acre | Percent control Giant Foxtail (weeks after treatment) 1 | 2 | Percent damage to soybeans (weeks after treatment) 1 | 2 |
|---|---|---|---|---|---|
| 1 | Cpd. A 0.125 lb/A | 93 | 98 | 0 | 0 |
| 2 | Cpd. A 0.125 lb/A bentazon 0.75 lb/A | 95 | 96 | 15 | 0 |
| 3 | Cpd. A 0.25 lb/A | 95 | 99 | 0 | 0 |
| 4 | Cpd. A 0.25 lb/A bentazon 0.75 lb/A | 99 | 100 | 8 | 0 |

TABLE 3

| Amount of active ingredients in lb/acre | Average % injury to soybeans |
|---|---|
| 0.75 lb bentazon (alone) | 6.7 |
| 0.75 lb bentazon; 0.125 lb fluazifop-butyl | 18.3 |
| 0.75 lb bentazon; 0.25 lb fluazifop-butyl | 35 |
| 0.75 lb bentazon; 0.5 lb fluazifop-butyl | 50 |
| 0.75 lb bentazon; 0.125 lb Cpd. A | 10 |
| 0.75 lb bentazon; 0.25 lb Cpd. A | 15 |
| 0.75 lb bentazon; 0.5 lb Cpd. A | 30 |
| 1.5 lb bentazon (Alone) | 16.6 |
| 1.5 lb bentazon; 0.125 fluazifop-butyl | 42 |
| 1.5 lb bentazon; 0.25 fluazifop-butyl | 60 |
| 1.5 lb bentazon; 0.5 fluazifop-butyl | 78 |
| 1.5 lb bentazon; 0.125 Cpd. A | 22 |
| 1.5 lb bentazon; 0.25 Cpd. A | 25 |
| 1.5 lb bentazon; 0.5 Cpd. A | 40 |

EXAMPLE 4

Substantially the same procedures as those described in Examples 1-3 were repeated except that 0.25% v/v ORTHO® X-77 brand surfactant was used as the surfactant. Additionally, 2-(4-((3-fluoro-5-(trifluoromethyl)-2-pyridinyl)oxy)phenoxy)propionic acid, methyl ester (hereinafter "Cpd. B") with BASAGRAN brand bentazon was applied to soybeans and evaluated for phytotoxicity toward soybean plants 6 days after treatment. Results are listed in Table 4.

TABLE 4

| Amount of active ingredients in lb/acre | Average % injury to soybeans |
|---|---|
| 0.75 lb bentazon (alone) | 10 |
| 0.75 lb bentazon; 0.125 lb fluazifop-butyl | 15 |
| 0.75 lb bentazon; 0.25 lb fluazifop-butyl | 25 |
| 0.75 lb bentazon; 0.5 lb fluazifop-butyl | 50 |
| 0.75 lb bentazon; (Alone) | 10 |
| 0.75 lb bentazon; 0.125 lb Cpd. A | 15 |
| 0.75 lb bentazon; 0.25 lb Cpd. A | 15 |
| 0.75 lb bentazon; 0.5 lb Cpd. A | 20 |
| 0.75 lb bentazon; (Alone) | 10 |
| 0.75 lb bentazon; 0.125 lb Cpd. B | 15 |
| 0.75 lb bentazon; 0.25 lb Cpd. B | 20 |
| 0.75 lb bentazon; 0.5 lb Cpd. B | 20 |
| 1.5 lb bentazon; (Alone) | 15 |
| 1.5 lb bentazon; 0.125 fluazifop-butyl | 30 |
| 1.5 lb bentazon; 0.25 fluazifop-butyl | 45 |
| 1.5 lb bentazon; 0.5 fluazifop-butyl | 55 |
| 1.5 lb bentazon; (Alone) | 15 |
| 1.5 lb bentazon; 0.125 Cpd. A | 20 |
| 1.5 lb bentazon; 0.25 Cpd. A | 25 |
| 1.5 lb bentazon; 0.5 Cpd. A | 35 |
| 1.5 lb bentazon; (Alone) | 15 |
| 1.5 lb bentazon; 0.125 Cpd. B | 20 |
| 1.5 lb bentazon; 0.25 Cpd. B | 25 |
| 1.5 lb bentazon; 0.5 Cpd. B | 40 |

The data of Table 4 above is conveniently placed in graphic form in Graph A below to visually illustrate the present invention.

GRAPH A

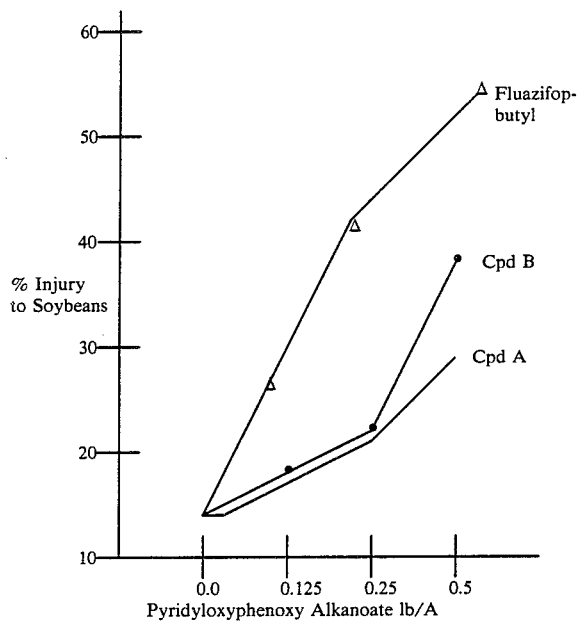

On repeating the procedures described in the above examples employing a combination of benzothiadiazinone herbicides and pyridyloxyphenoxy alkanoate herbicides containing a substituent other than hydrogen in the 3-position of the pyridine ring, substantially the same results are obtained, i.e., less damage to soybean plants when compared to the combination of benzothiadiazinones and pyridyloxyphenoxy alkanoates having hydrogen as the substituent in the 3-position of the pyridine ring.

In further embodiments, the broad spectrum herbicidal compositions of the present invention can be advantageously employed in combination with one or more additional pesticidal compounds. Such additional pesticidal compounds may be insecticides, nematocides, arthropodicides, herbicides, fungicides or bactericides that are compatible with the compositions of the present invention and non-phytotoxic to soybeans when applied thereto. Accordingly, in such embodiments, the additional pesticidal compounds are employed as supplemental toxicants for the same or for different pesticidal uses, or as additaments.

I claim:

1. In a method of selectively controlling broadleaf weeds and grassy weeds postemergently in a soybean crop by application of a herbicidally effective amount of a combination of a pyridyloxy(or thio)phenoxy propionic acid or an agriculturally acceptable salt, amide or, ester thereof active as a grass herbicide and 3-(1-methylethyl)-1H-2,1,3-benzothiadiazin-4(3H)-one-2,2-dioxide or an analog thereof having in the 8-position chloro, bromo, fluoro, alkyl of 1 to 8 carbon atoms or nitro, or, a salt thereof, active as a broadleaf weed herbicide, wherein the improvement comprises employing as the pyridyloxy(or thio)phenoxy propionic acid or salt, amide or ester thereof a 2-(4-(2-pyridyloxy(or thio))-phenoxy)propionic acid or salt, amide or ester thereof having in the 3-position of the pyridine ring a substituent selected from the group consisting of Cl, F, Br, I, $CF_3$, $C_1$-$C_4$ alkyl, $C_1$-$C_4$ alkoxy and $NO_2$, the propionic acid or salt, amide or ester being applied at a rate in the range of about 0.03 to about 0.5 pounds per acre and the benzothiadiazinone compound being applied at a rate in the range of about 0.5 to about 1.5 pounds per acre, whereby substantially less damage to the soybean plants is exhibited than occurs when the pyridyloxy(or thio)phenoxy propionic acid or salt, amide or ester thereof has hydrogen in the 3-position of the pyridine ring.

2. The method of claim 1 wherein said pyridyloxy(or thio)phenoxy propionic acid or an agriculturally acceptable salt, amide or ester thereof is a pyridyloxyphenoxy propionic acid compound having chloro or fluoro as the substituent in the 3-position of the pyridine ring.

3. The method of claim 2 wherein said pyridyloxyphenoxy propionic acid compound is [2-(4-(3-chloro-5-(trifluoromethyl)-2-pyridinyl)oxy)phenoxy propionic acid] 2-(4-((3-chloro-5-(trifluoromethyl-2-pyridyl)oxy)-phenoxy)propionic acid or an agriculturally acceptable salt, alcohol, ester or amide thereof.

4. The method of claim 3 wherein said pyridyloxyphenoxy propionic acid compound is a butyl, methyl or ethoxyethyl ester of 2-(4-((3-chloro-5-(trifluoromethyl)-2-pyridyl)oxy)phenoxy)-propionic acid.

5. The method of claim 4 wherein said ester is the butyl ester.

6. The method of claim 4 wherein said ester is the methyl ester.

7. The method of claim 4 wherein said ester is the ethoxyethyl ester.

8. The method of claim 2 wherein said pyridyloxy(or thio)phenoxy propionic acid compound is 2-(4-((3-fluoro-5-(trifluoromethyl)-2-pyridyl)oxy)phenoxy)propionic acid or an agriculturally acceptable salt, ester or amide thereof.

9. The method of claim 8 wherein said pyridyloxyphenoxy propionic acid compound is a butyl, methyl or ethoxyethyl ester of 2-(4-((3-fluoro-5-(trifluoromethyl)-2-pyridyl)oxy)phenoxy)propionic acid.

10. The method of claim 9 wherein said ester is the methyl ester.

11. The method of claim 8 wherein the benzothiadiazinone compound is bentazon.

12. The method of claim 2 wherein said pyridyloxy(or thio)phenoxy propionic acid compound is 2-(4-((3-chloro-5-(trifluoromethyl)-2-pyridyl)oxy)phenoxy)propionic acid or an agriculturally acceptable salt, ester or amide thereof.

13. The method of claim 12 wherein the benzothiadiazinone compound is bentazon.

14. The method of claim 13 wherein the propionic acid compound is an ester.

* * * * *

UNITED STATES PATENT AND TRADEMARK OFFICE
CERTIFICATE OF CORRECTION

PATENT NO. : 4,586,949

DATED : May 6, 1986

INVENTOR(S) : B. Clifford Gerwick III

Page 1 of 2

It is certified that error appears in the above-identified patent and that said Letters Patent is hereby corrected as shown below:

Col. 2, line 16, that portion of the sentence reading "-5-(trifluoromethy )" should read -- -5-(trifluoromethyl) --.

Col. 7, the graph should read as follows:

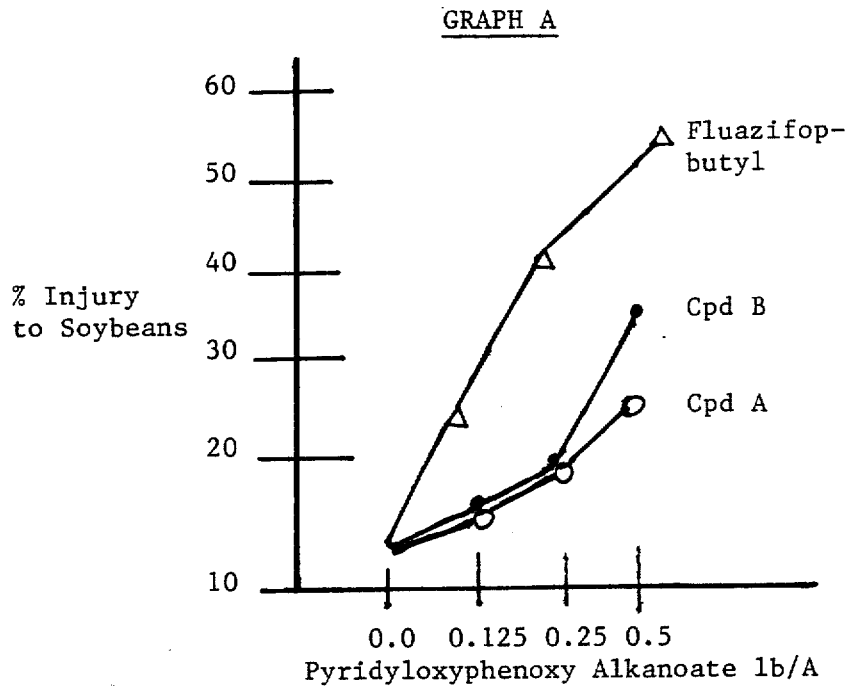

UNITED STATES PATENT AND TRADEMARK OFFICE
CERTIFICATE OF CORRECTION

PATENT NO. : 4,586,949

DATED : May 6, 1986

INVENTOR(S) : B. Clifford Gerwick III

It is certified that error appears in the above-identified patent and that said Letters Patent is hereby corrected as shown below:

Col. 7, line 57, the comma should be deleted after the word "or".

Signed and Sealed this

Third Day of March, 1987

Attest:

DONALD J. QUIGG

*Attesting Officer*  *Commissioner of Patents and Trademarks*